US012773321B2

(12) United States Patent
Lauf et al.

(10) Patent No.: US 12,773,321 B2
(45) Date of Patent: Oct. 27, 2026

(54) EXPANDABLE IMPLANT WITH PIVOTING CONTROL ASSEMBLY

(71) Applicant: Life Spine, Inc., Huntley, IL (US)

(72) Inventors: Garrett Lauf, Hampshire, IL (US); Brett Nowak, Lake in the Hills, IL (US); Daniel Predick, Wheat Ridge, CO (US); Paul Christopher Zakelj, Chicago, IL (US)

(73) Assignee: LIFE SPINE, INC., Huntley, IL (US)

( * ) Notice: Subject to any disclaimer, the term of this patent is extended or adjusted under 35 U.S.C. 154(b) by 0 days.

(21) Appl. No.: 19/254,842

(22) Filed: Jun. 30, 2025

(65) Prior Publication Data

US 2025/0325377 A1 Oct. 23, 2025

Related U.S. Application Data

(63) Continuation of application No. 17/990,101, filed on Nov. 18, 2022, now Pat. No. 12,364,610, which is a continuation of application No. 17/014,546, filed on Sep. 8, 2020, now Pat. No. 11,554,020.

(51) Int. Cl.
*A61F 2/44* (2006.01)
*A61F 2/30* (2006.01)

(52) U.S. Cl.
CPC .......... *A61F 2/442* (2013.01); *A61F 2/30744* (2013.01); *A61F 2002/30224* (2013.01); *A61F 2002/30405* (2013.01); *A61F 2002/30528* (2013.01); *A61F 2002/30538* (2013.01)

(58) Field of Classification Search
CPC .......... A61F 2/44; A61F 2/4455; A61F 2/442; A61F 2/4425; A61F 2002/443
See application file for complete search history.

(56) References Cited

U.S. PATENT DOCUMENTS

| | | | | |
|---|---|---|---|---|
| 6,176,882 B1 * | 1/2001 | Biedermann | A61F 2/447 623/17.11 |
| 6,478,823 B1 * | 11/2002 | Michelson | A61F 2/442 623/17.11 |
| 12,433,763 B2 * | 10/2025 | Blain | A61F 2/447 |
| 2016/0120660 A1 * | 5/2016 | Melkent | A61F 2/447 623/17.16 |
| 2019/0336301 A1 | 11/2019 | Engstrom | |
| 2021/0401586 A1 * | 12/2021 | Zakelj | A61F 2/447 |

* cited by examiner

*Primary Examiner* — Matthew J Lawson
(74) *Attorney, Agent, or Firm* — Foley & Lardner LLP

(57) ABSTRACT

An expandable implant includes a lower support; an upper support pivotally coupled to the lower support and including a control channel; and a control assembly. The control assembly includes a control shaft coupled to the lower support and a control member coupled to the control shaft and configured to move along the control shaft. The control member includes a base member and a pivot member pivotally coupled to the base member, the pivot member configured to move within the control channel. Movement of the control member along the control shaft causes the pivot member to pivot relative to the base member, and the upper support to pivot relative to the lower support.

20 Claims, 7 Drawing Sheets

EXPANDABLE IMPLANT WITH PIVOTING CONTROL ASSEMBLY

CROSS-REFERENCE TO RELATED PATENT APPLICATIONS

This application is a continuation of U.S. patent application Ser. No. 17/990,101, filed Nov. 18, 2022, which is a continuation of U.S. patent application Ser. No. 17/014,546, filed Sep. 8, 2020, all of which are incorporated herein by reference in their entireties.

BACKGROUND

The present disclosure relates generally to expandable implants usable in connection with the spine or other parts of the human anatomy. Certain implants are expandable, in that the implants may, for example, have a variable height dependent upon a degree of expansion.

SUMMARY

At least one embodiment relates to an expandable implant. The expandable implant includes a lower support; an upper support pivotally coupled to the lower support and including a control channel; and a control assembly. The control assembly includes a control shaft coupled to the lower support; and a control member coupled to the control shaft and configured to move along the control shaft. The control member includes a base member and a pivot member pivotally coupled to the base member, the pivot member configured to move within the control channel. Movement of the control member along the control shaft causes the pivot member to pivot relative to the base member, and the upper support to pivot relative to the lower support.

Another embodiment relates to an expandable implant. The expandable implant includes a first support; an second support pivotally coupled to the first support; a control shaft rotatably coupled to the first support; and a control member coupled to the control shaft and configured to move along the control shaft such that movement of the control member along the control shaft cause pivotal movement of the second support relative to the first support, a portion of the control member configured to rotate relative to the second support as the control member moves along the control shaft.

Another embodiment relates to an expandable implant. The implant includes a lower support having a first lower surface, a first upper surface, an access bore configured to receive an expansion tool, and an inner housing that defines a central aperture extending between the first lower surface and the first upper surface, an upper support having a second upper surface, a second lower surface, a control channel, and a rear aperture extending between the second upper surface and the second lower surface, wherein the upper support is pivotally coupled to the lower support, the implant is configured to expand between a first, collapsed position and a second, expanded position such that pivotal movement of the upper support relative to the lower support changes an angle defined between the first lower surface and the second upper surface as the implant expands, and at least a portion of the inner housing is received by the rear aperture the first, collapsed position, a control shaft rotatably coupled to the lower support, wherein the control shaft includes a head configured to receive the expansion tool, wherein manipulation of the expansion tool causes the implant to expand, and wherein the central aperture is located between the head and the access bore, and a control member threadingly coupled to the control shaft, the control member includes a base member threadingly coupled to the control shaft and rotatably fixed relative to the lower support, a first pivot member pivotally coupled to a first side of the base member and slidingly received in the control channel, a second pivot member pivotally coupled to a second side of the base member opposite the first side and slidingly received in the control channel.

This summary is illustrative only and is not intended to be in any way limiting. Other aspects, inventive features, and advantages of the devices or processes described herein will become apparent in the detailed description set forth herein, taken in conjunction with the accompanying figures, wherein like reference numerals refer to like elements.

DETAILED DESCRIPTION

Figure 1:
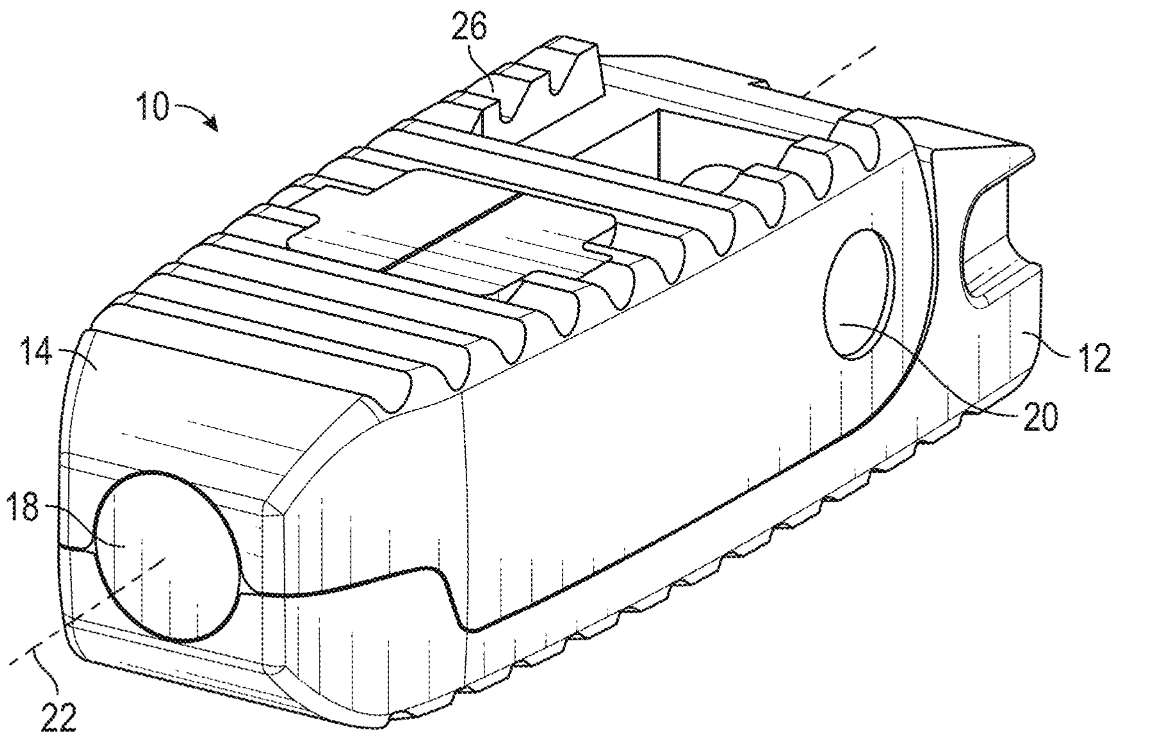
FIG. 1 is a perspective view of an implant in a collapsed position according to one embodiment.

Before turning to the figures, which illustrate certain exemplary embodiments in detail, it should be understood that the present disclosure is not limited to the details or methodology set forth in the description or illustrated in the figures. It should also be understood that the terminology used herein is for the purpose of description only and should not be regarded as limiting.

Referring generally to the figures, various embodiments of an expandable implant are disclosed herein. The expandable implant may be usable in connection with the spine (e.g., between vertebral bodies) or other parts of the human body. In some embodiments, the implant provides a lumbar interbody expandable implant that expands in a lordotic fashion. The implant may include an upper support hingedly or pivotally coupled to a lower support, such that an amount of lordosis provided by the implant can be adjusted as desired. A control assembly may include a control shaft and a control member mounted to the control shaft. One or more pivoting members are pivotally coupled to the control member and move within one or more control channels in the upper implant. In one embodiment, rotation of the control shaft causes translation of the control member along the control shaft relative to the lower support. As the control member translates, ramp surfaces on the pivoting member(s) slidingly engage corresponding ramp surface(s) on the upper support to cause expansion or contraction of the implant (e.g., to move the implant between a collapsed position and an expanded position, and intermediate positions therebetween).

The implants disclosed herein may be made of any suitable materials, including a variety of metals, plastics, composites, or other suitable bio-compatible materials. In some embodiments, some or all of the components of the implants disclosed herein may be made of the same material, while in other embodiments, different materials may be used for different components.

Referring now to FIGS. 1-8, an expandable implant 10 is shown according to one embodiment. Implant 10 is usable, for example, between and/or within portions of bone (e.g., between and/or within vertebral bodies or the spine or other portions of bone). In one embodiment, implant 10 includes a lower support 12 (e.g., a base support or assembly, a foundational plate, endplate, or member, etc.) and an upper support 14 (e.g., an adjustable support or assembly, a hinged plate, endplate, or member, etc.) adjustably coupled to the lower support 12 by way of a control assembly 16 (e.g., an adjustment assembly, etc.) and one or more pivot pins 20. In some embodiments, upper support 14 pivots relative to lower support 12 as a result of user manipulation of control assembly 16 (e.g., as a result of rotation or movement of a control shaft or member, etc.). In one embodiment, upper support 14 expands relative to lower support 12 in a lordotic fashion to mimic the natural curvature of the human spine. The amount of lordosis can be increased or decreased by manipulation of control assembly 16. An end cap 18 (e.g., a distal end member, etc.) assists in maintaining control assembly 16 in a desired position. Pivot pins 20 extend at least partially through lower support 12 and upper support 14 to enable relative pivoting adjustment between upper support 14 and lower support 12.

Figure 2:
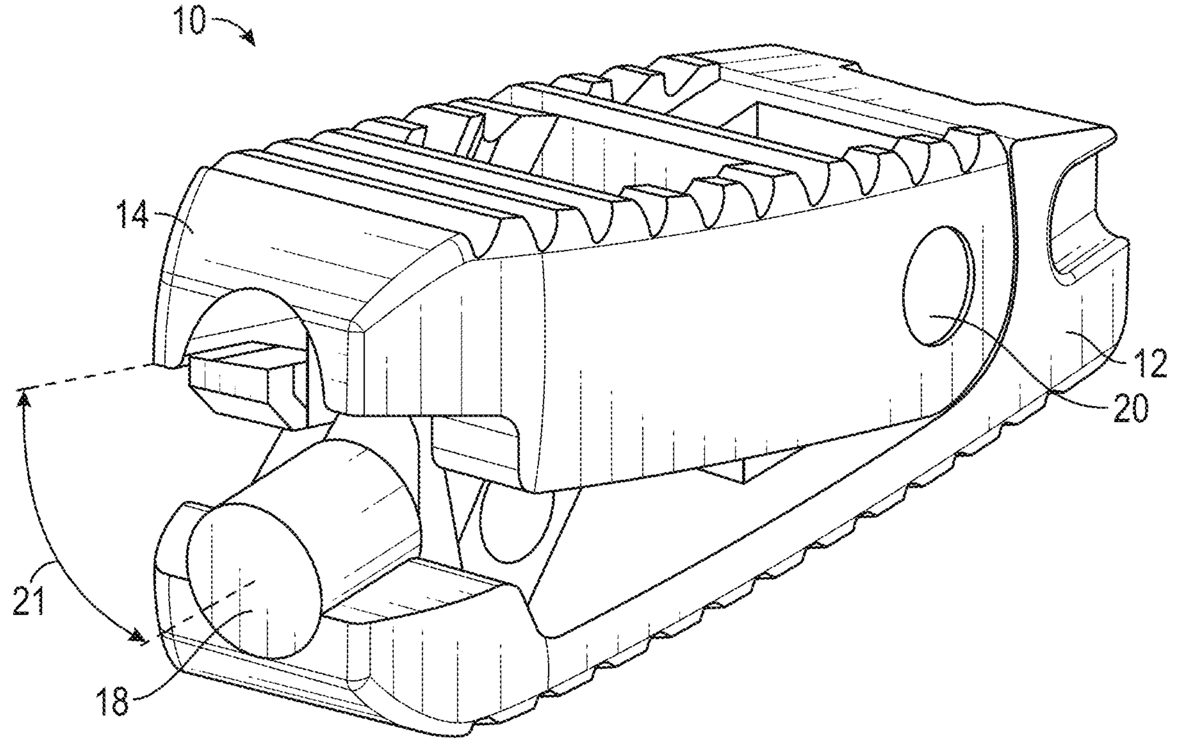
FIG. 2 is a perspective view of the implant of FIG. 1 in an expanded position according to one embodiment.
Figure 3:
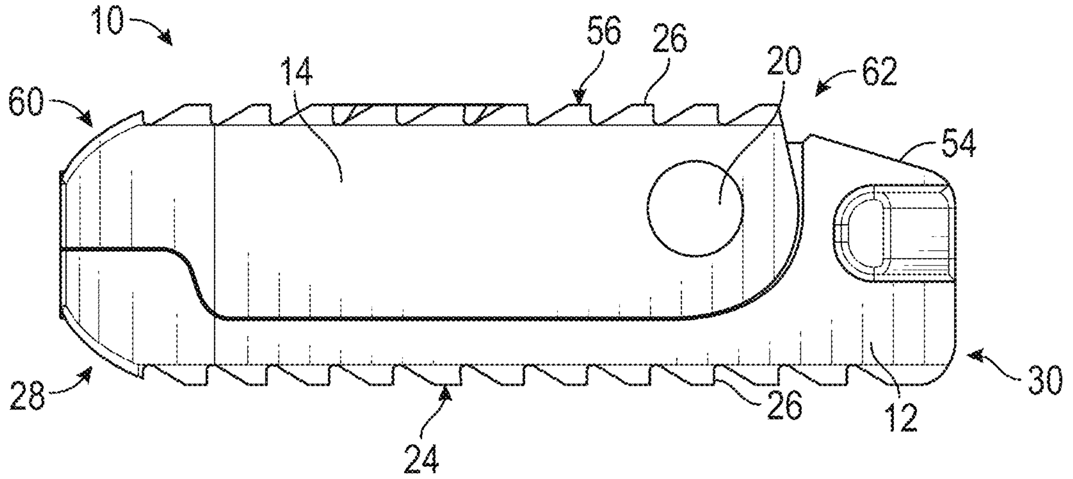
FIG. 3 is a side view of the implant of FIG. 1 in the collapsed position according to one embodiment.
Figure 4:
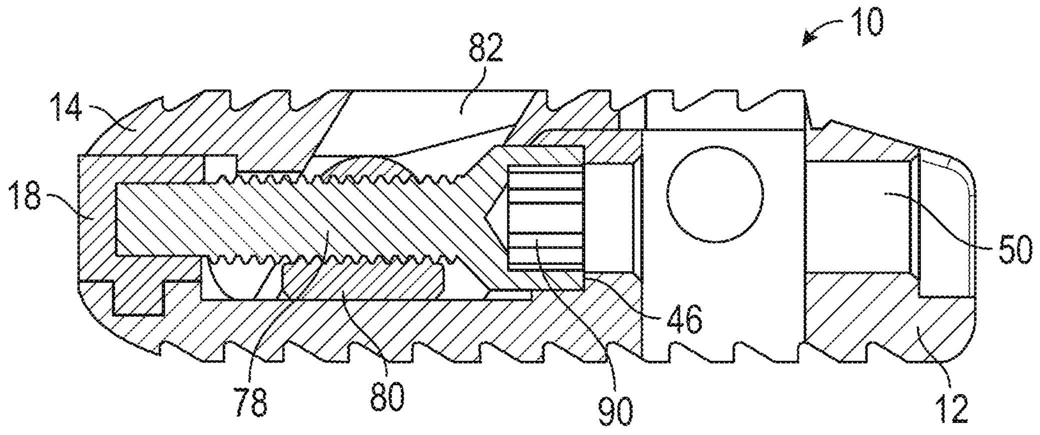
FIG. 4 is a cross-section view of the implant of FIG. 1 in a collapsed position according to one embodiment.
Figure 5:
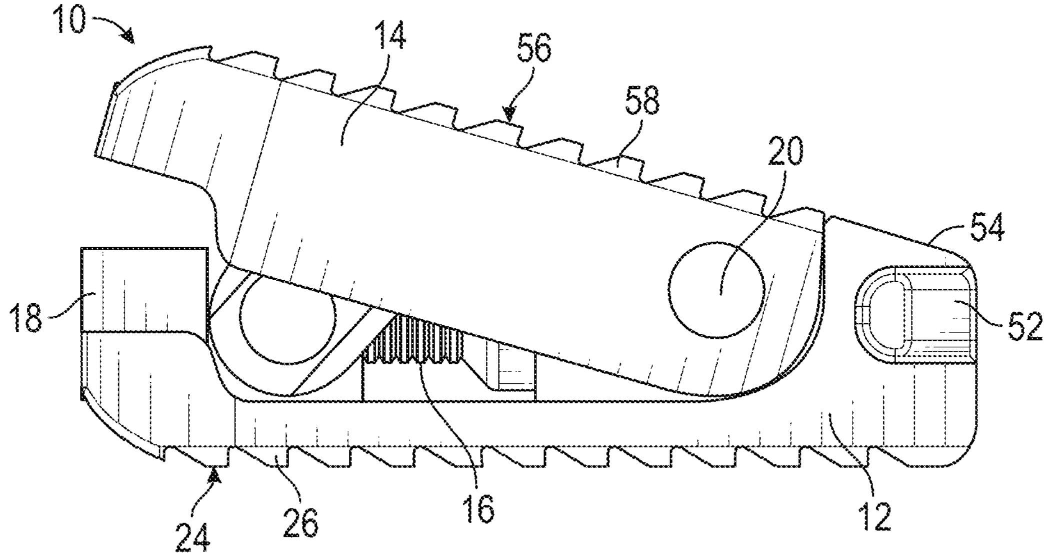
FIG. 5 is a side view of the implant of FIG. 1 in an expanded position according to one embodiment.
Figure 6:
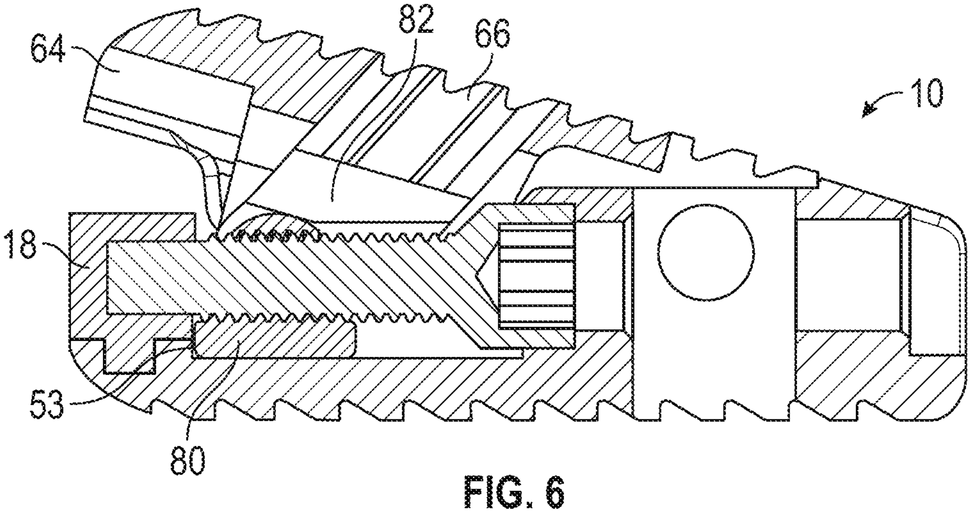
FIG. 6 is a side view of the implant of FIG. 1 in an expanded position according to one embodiment.
Figure 7:
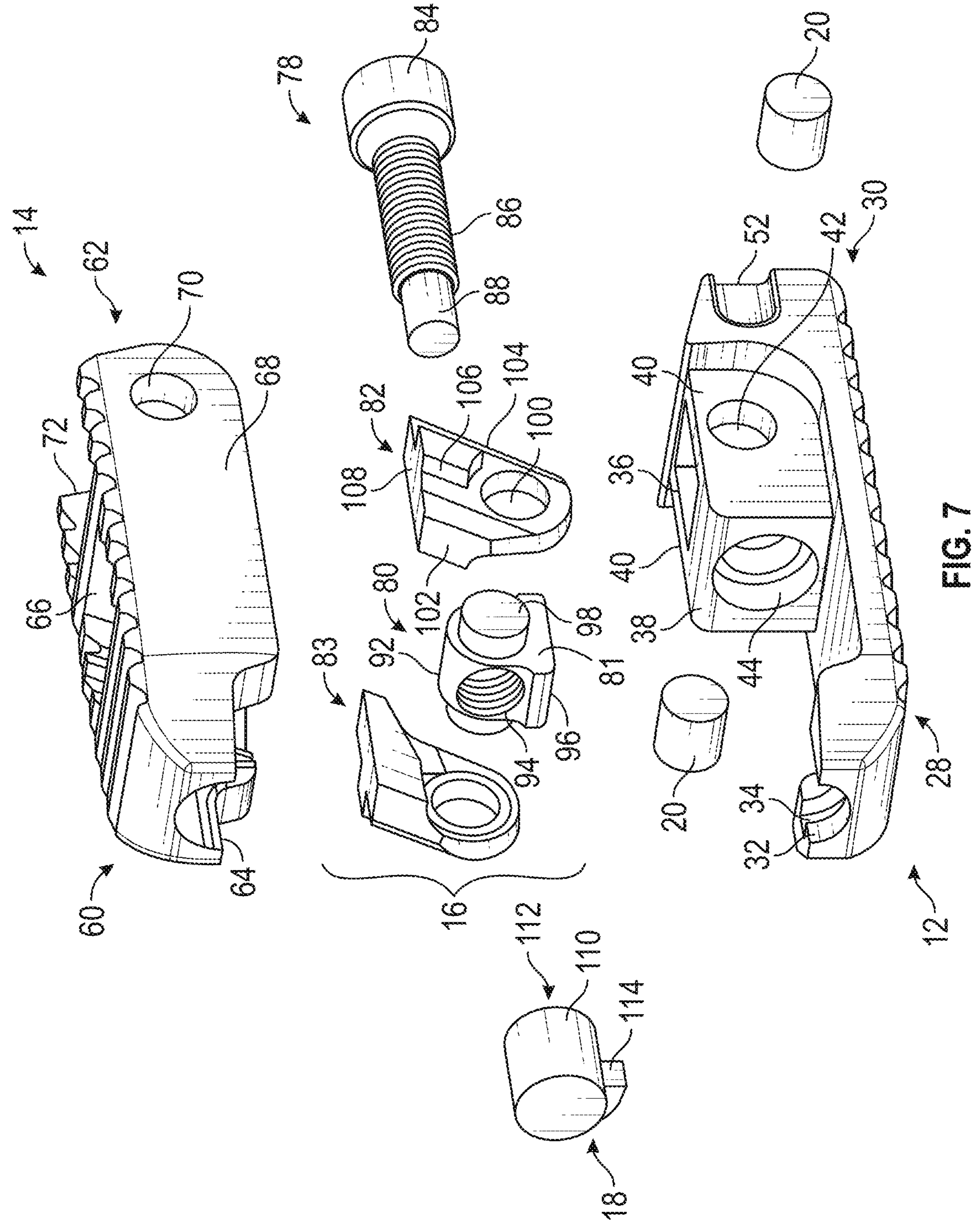
FIG. 7 is an exploded view of the implant of FIG. 1 according to one embodiment.
Figure 8:
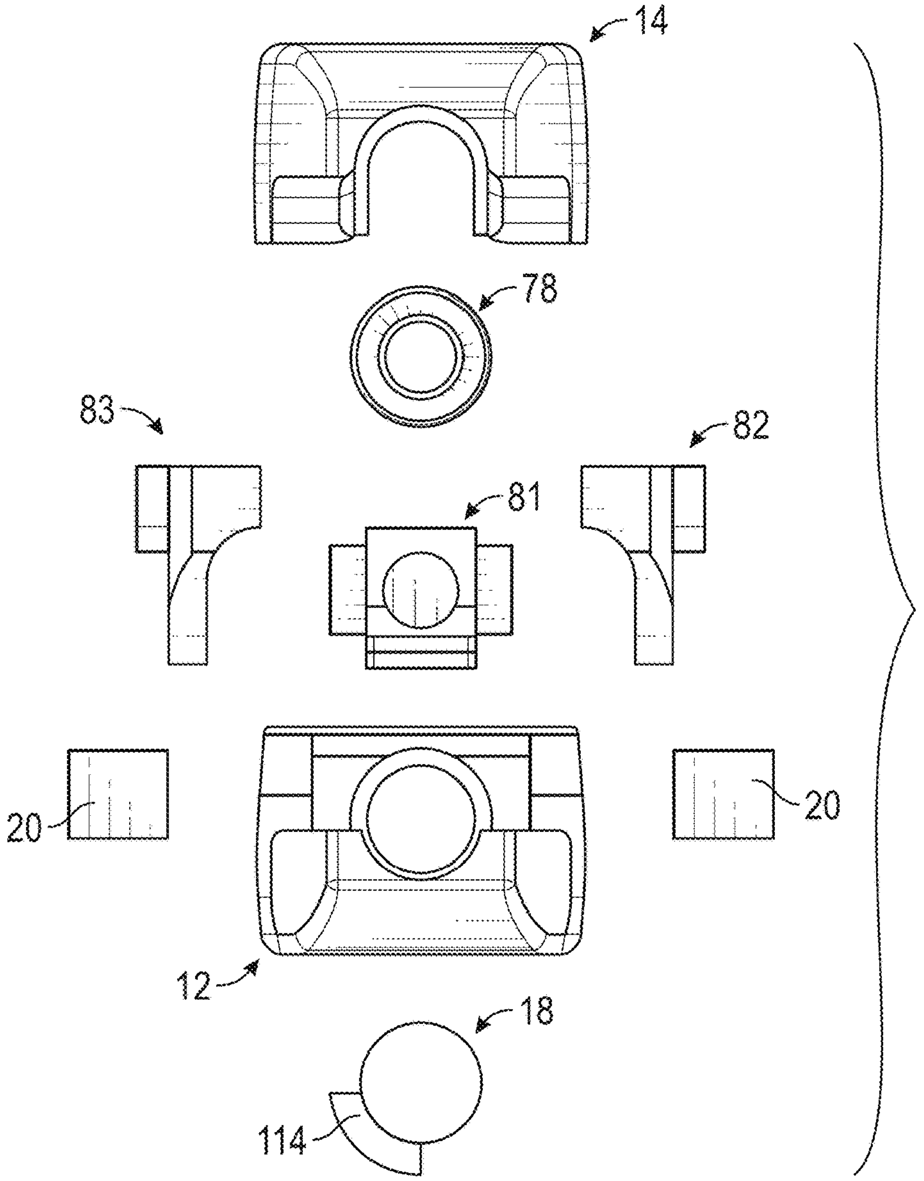
FIG. 8 is another exploded view of the implant of FIG. 1 according to one embodiment.

Implant 10 is movable between a collapsed position, as shown, for example, in FIGS. 1, 3, and 4, and an expanded position, as shown, for example, in FIGS. 2, 5, and 6. Further, implant 10 may be adjusted to any intermediate position between a fully collapsed position and a fully expanded position. Further yet, the amount of total expansion, (e.g., the maximum expansion angle 21 relative to axis 22 shown in FIGS. 1 and 2) may be varied to suit a particular application.

According to one embodiment, lower support 12 extends between a distal end 28 and a proximal end 30 and includes a bottom surface 24 having a plurality of ridges 26 (e.g., teeth, etc.) formed by corresponding grooves or channels. Ridges 26 are configured to facilitate gripping of adjacent portions of bone. A lower distal recess 32 is provided at distal end 28, and a retention groove 34 extends from lower distal recess 32. Retention groove 34 is configured to receive a retention projection 114 of end cap 18, as discussed in greater detail elsewhere herein. In some embodiments, lower support 12 includes an inner housing 36. Inner housing 36 is defined by a front wall 38 and side walls 40 that extend from front wall 38 toward proximal end 30 of lower support 12. Inner housing 36 in some embodiments defines a central aperture 48 (e.g., a cavity, etc.) providing access to an interior of implant 10. Central aperture 48 may be configured to receive bone growth material and/or bone material from adjacent portions of bone.

Lower support 12 further includes an access bore 50, tool recesses 52, and an inclined surface 54. Access bore 50 (see FIG. 4) provides access to central aperture 48 (e.g., for delivery of bone growth or other material) and control assembly 16 (e.g., to enable manipulation of control assembly 16 and control of the expansion and/or contraction of implant 10). Tool recesses 52 are configured to receive one or more tool portions to enable positioning of implant 10 in a desired position (e.g., within an intervertebral space, etc.). Inclined surface 54 (see FIG. 5) is in one embodiment configured such that when implant 10 is in an expanded configuration, inclined surface 54 is aligned with (e.g., substantially coplanar with) a top surface 56 of upper support 14 to provide additional support to adjacent portions of bone. In some embodiments, inclined surface 54 is angled downward in a proximal direction relative to a top surface 56 of upper support 14 when implant 10 is in a collapsed position. The angular position of inclined surface 54 is in some embodiments intended to accommodate the natural curvature of the human spine.

According to one embodiment, upper support 14 extends between a distal end 60 and a proximal end 62 and includes a top surface 56 having a plurality of ridges 58 (e.g., teeth, etc.) formed by corresponding grooves or channels. Ridges 58 are configured to facilitate gripping of adjacent portions of bone. An upper distal recess 64 is provided at distal end 60 and receives end cap 18. Sidewalls 68 extend downward relative to top surface 56.

In one embodiment, upper support 14 includes two opposing sidewalls 68. Each sidewall 68 includes a pivot pin aperture 70 configured to receive a pivot pin 20 there through to enable pivoting movement of upper support 14 relative to lower support 12. Upper support 14 also includes a rear aperture or cavity 72 that receives all or a portion of inner housing 36 when implant 10 is a collapsed position. A control aperture 66 extends through upper support 14 and is defined at least partially by distal ramp surfaces 74 and proximal ramp surfaces 76. An alignment channel 77 extends along each sidewall 68 and along control aperture 66. As discussed in further detail below, control aperture 66 receives portions of control assembly 16, and the angle of control aperture 66 relative to axis 22 may be designed to provide a desired rate of pivoting of upper support 14 relative to lower support 12.

In one embodiment, control assembly 16 includes a control shaft 78, a control member 80, and one or more pivot members 82. In some embodiments, control assembly 16 includes a pair of pivot members 82, 83 positioned on opposite sides of control member 80. Control shaft 78 is rotatable or otherwise manipulatable to cause translation or movement of control member 80 along control shaft 78. As control member 80 moves along control shaft 78, pivot members 82 move within control aperture 66 (see FIG. 6) to change the angular position of upper support 144 relative to lower support 12.

Control shaft 78 includes a head 84, a threaded portion 86, an end portion 88 and a receiver 90 provided in head 84. Head 84 defines a first end of control shaft 78 and end portion 88 defines a second opposite end of control shaft 78, with threaded portion 86 provided there between. Head 84 is received in a control member bore 44 and engages a shoulder 46 to limit proximal movement of control shaft 78 during use of implant 10. End portion 88 is received by end cap 18 to limit distal movement of control shaft 78.

Control member 80 is received on control shaft 78. In one embodiment, control member 80 includes a base member 81 and one or more pivot members 82. In some embodiments, control member 80 includes first and second pivot members 82, 83 pivotally coupled to opposite sides of base member 81.

Base member 81 includes a central portion 92 having a threaded bore 94 that threadingly engages threaded portion 86 of control shaft 78. Base member 81 further includes a bottom 96 and a pair cylindrical pivot bosses 98. Due to the threaded engagement of base member 81 onto control shaft 78, rotation of control shaft 78 causes movement (e.g., translational movement) of base member 81 along control shaft 78.

In one embodiment, each pivot member 82, 83 includes a pivot aperture 100 that receives one of the pivot bosses 98 to enable pivoting movement of pivot members 82, 83 relative to base member 81 about pivot bosses 98. Pivot member 82, 83 are mirror images of each other in one embodiment, and as such, pivot member 82 will be described in detail, with the understanding that pivot member 83 shares similar features. For example, pivot member 83 may include an alignment guide 107 that is similar to alignment guide 106.

Pivot member 82 includes distal ramp surface 102, proximal ramp surface 104, alignment guide 106, and top surface 108. Distal ramp surface 102 of pivot member 82 slidingly engages distal ramp surface 74 of upper support 14. Similarly, proximal ramp surface 104 of pivot member 82 slidingly engages proximal ramp surface 76 of upper support 14. During movement of base member 81 along control shaft 78, pivot members 82, 83 pivot about pivot bosses 98 as the corresponding distal and proximal ramp surfaces of the pivot members 82, 83 and upper support 14 engage, causing upper support 14 to move relative to lower support 12, and implant 10 to move toward an expanded or collapsed position, depending on the direction of rotation of control shaft 78.

Alignment guide 106 of pivot member 82 is received within alignment channel 77 of upper support 14 to maintain proper alignment between components and facilitate movement of upper support 14 relative to lower support 12. In some embodiments, when implant 10 is in a collapsed position, top surface 108 of pivot member 82 is generally aligned with top surface 56 of upper support 14. In some embodiments, top surface 108 may be substantially smooth, while in other embodiments, top surface 108 may be textured, include teeth or groves, or have other surface features.

End cap 18 includes a main body 110, a control shaft bore 112, and a retention projection 114. Control shaft bore 112 receives end portion 88 of control shaft 78. Retention projection 114 is received in retention groove 34 in lower support 12 to retain end cap 18 in place. In one embodiment, end cap 18 is rotated approximately 90 degrees to properly seat retention projection 114 within retention groove 34.

According to one embodiment, during use, a user positions implant 10 into a desired position, such as an intervertebral space, while collapsed, as shown, for example, in FIG. 1. To reposition implant 10, an appropriate tool may engage tool recesses 52 on lower support 12. In some embodiments, implant 10 is inserted into a space distal end first, with the appropriate tool engaging the proximal end of implant 10.

If desired, implant 10 may then be expanded to provide, for example, a desired amount of lordosis. Implant 10 may be expanded to a fully expanded position, or any intermediate expanded position between the fully collapsed position and the fully expanded position. In order to expand implant 10, in some embodiments, a user inserts an appropriate expansion tool through access bore 50 in lower support 12 and into receiver 90 in head 84 of control shaft 78. The expansion tool may then be used to manipulate the control shaft 78 to cause expansion of the implant 10. For example, receiver 90 may be hexagonal shaped, and the tool may be a hexagonal driver. Other suitable receivers and tools may be used according to various alternative embodiments.

As control shaft 78 is rotated, control member 80 translates along control shaft 78. For example, in one embodiment, to expand implant 10, control member 80 moves toward the distal end of lower support 12 as shown in FIGS. 4 and 6. Bottom 96 of base member 80 rides along a surface of lower support 12, and the travel of control member 80 is limited by limit shoulder 53, as shown in FIG. 6. In some embodiments, shoulder 53 is integrally formed (e.g., molded, etc.) with a remaining portion of lower support 12 to provide sufficient support for control shaft 78 during expansion of implant 10.

As control member 80 moves along control shaft 78, ramp surfaces on pivot members 82, 83 engage ramp surfaces of upper support 14 and cause upper support 14 to rotate about pivot pins 20. As upper support 14 pivots relative to lower support 12, pivot members 82 pivot about pivot bosses 98 on base member 81 to maintain proper alignment between the ramp surfaces on pivot members 82, 83 and the ramp surfaces on upper support 14.

In some embodiments and as shown in the FIGURES, the pivoting features of upper support 14 and pivot members 82, 83 maintain a generally parallel relationship between ramp surfaces 74, 76 of upper support 14 and ramp surfaces 102, 104 of pivot members 82, 83, which may facilitate the wedging action required to move upper support 14 relative to lower support 12.

If it is desirable to move implant 10 toward the collapsed position, control shaft 78 is rotated in an opposite direction from that used during expansion of implant 10. In one embodiment, to collapse implant 10, control member 80 moves toward the proximal end of lower support as shown in FIGS. 4 and 6. As control member 80 moves along control shaft 78, ramp surfaces on pivot members engage ramp surfaces of upper support 14 and cause upper support 14 to rotate about pivot pins 20.

Figure 9:
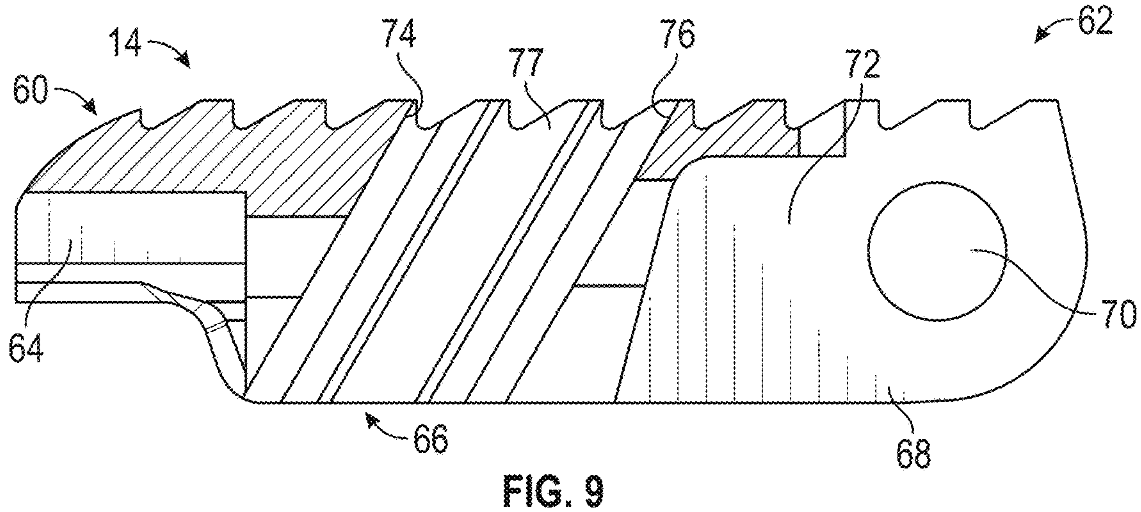
FIG. 9 is a side cross-section view of an upper support of the implant of FIG. 1 according to one embodiment.

Referring now to FIG. 9, a cross-section view of the upper support 14 is shown according to an example embodiment. As shown, the upper support 14 includes a control aperture 66 configured to receive the pivot member 83. For example, the alignment guide 107 of the pivot member 83 may slide within the alignment channel 77 of the control aperture 66 as the implant 10 expands. Further, the distal ramp surface 74 and the proximal ramp surface 76 may interface with the ramp surfaces of the pivot member 83 when the implant 10 expands. The angle of expansion (e.g., angle 21) and the rate of angular expansion may be customized by altering the angles of the ramp surfaces 74, 76 and the alignment channel 77. It should be appreciated that the upper support 14 may also include a second control aperture 77 opposite the control aperture 66 configured to receive the pivot member 82 in a similar manner (see FIG. 10). The upper support 14 is also shown include a pivot pin aperture 70 configured to receive a pivot pin 20 there through to enable pivoting movement of upper support 14 relative to lower support 12.

Figure 10:
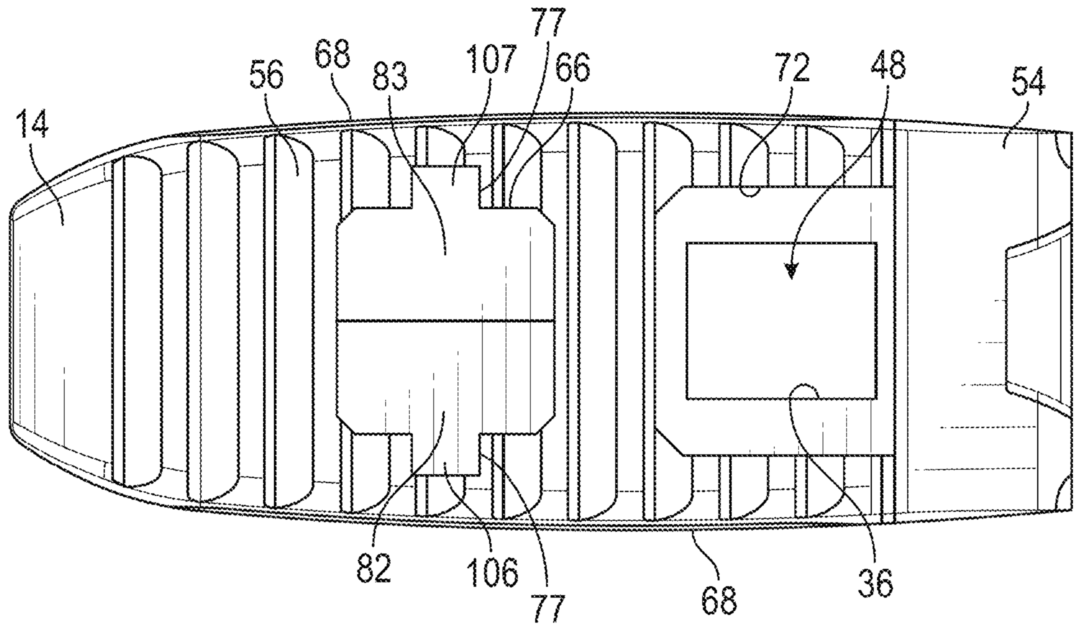
FIG. 10 is a top view of the implant of FIG. 1 according to one embodiment.
Figure 11:
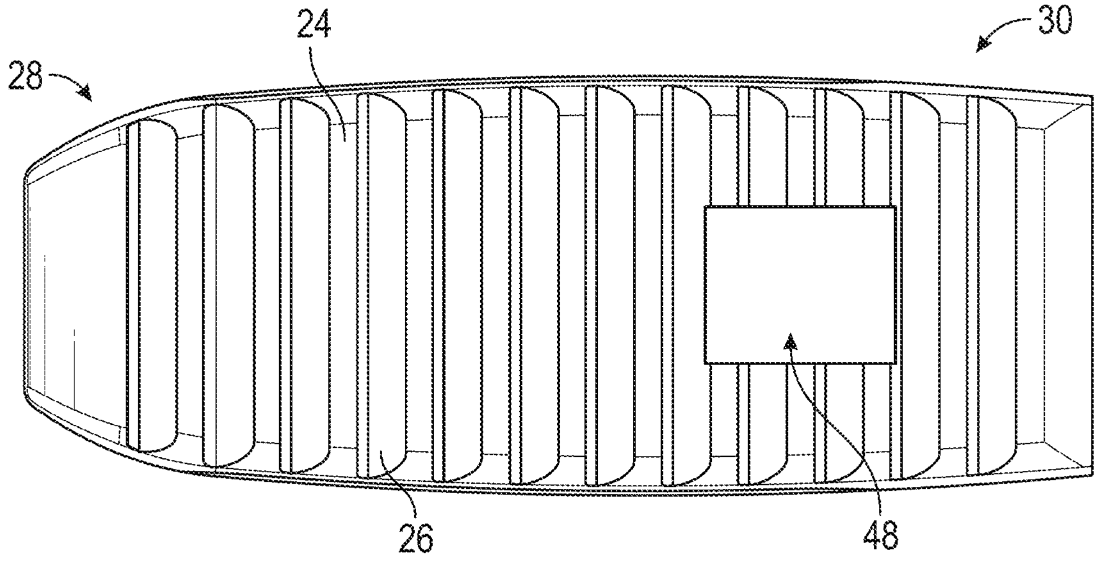
FIG. 11 is a bottom view of the implant of FIG. 1 according to one embodiment.

Referring now to FIGS. 10 and 11, a top view and a bottom view, respectively, of the implant 10 is shown according to an example embodiment. As shown, pivot member 83 includes an alignment guide 107 that is received by the first alignment channel 77 in the upper support 14. Further, pivot member 82 includes an alignment guide 106 that is received by the second alignment channel 77 in the upper support. Further, as shown, the rear aperture 72 of the upper support 14 also receives all or a portion of the inner housing 36. The inner housing 36 further defines the central aperture 48 (e.g., a cavity, etc.) providing access to an interior of implant 10 from the top surface 56 of the upper support and from the bottom surface 24 of the lower support 12. Central aperture 48 may be configured to receive bone growth material and/or bone material from adjacent portions of bone.

Figure 12:
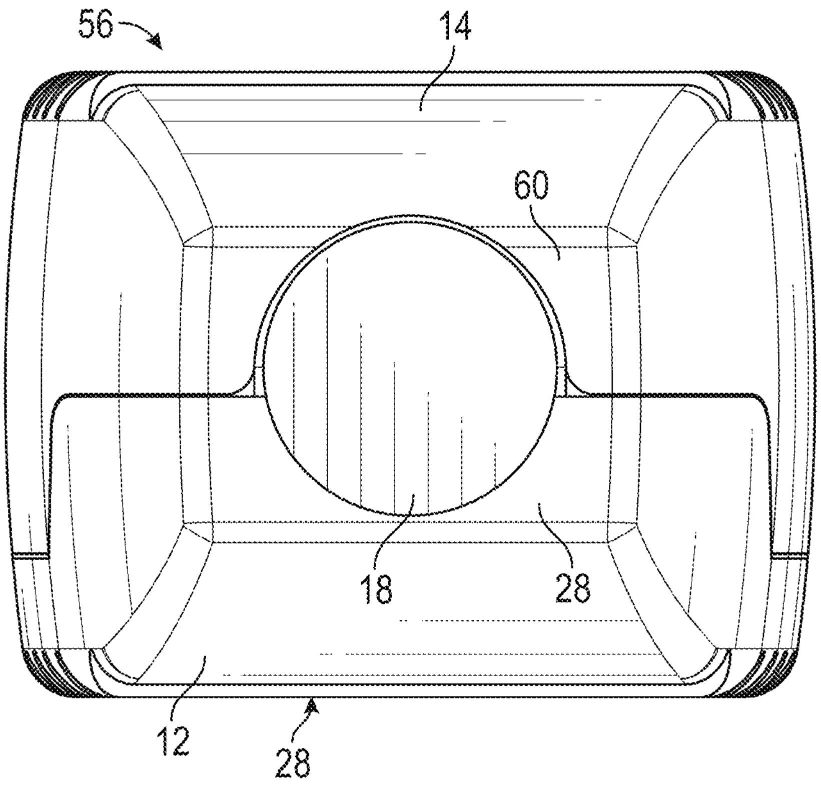
FIG. 12 is a front view of the implant of FIG. 1 according to one embodiment.
Figure 13:
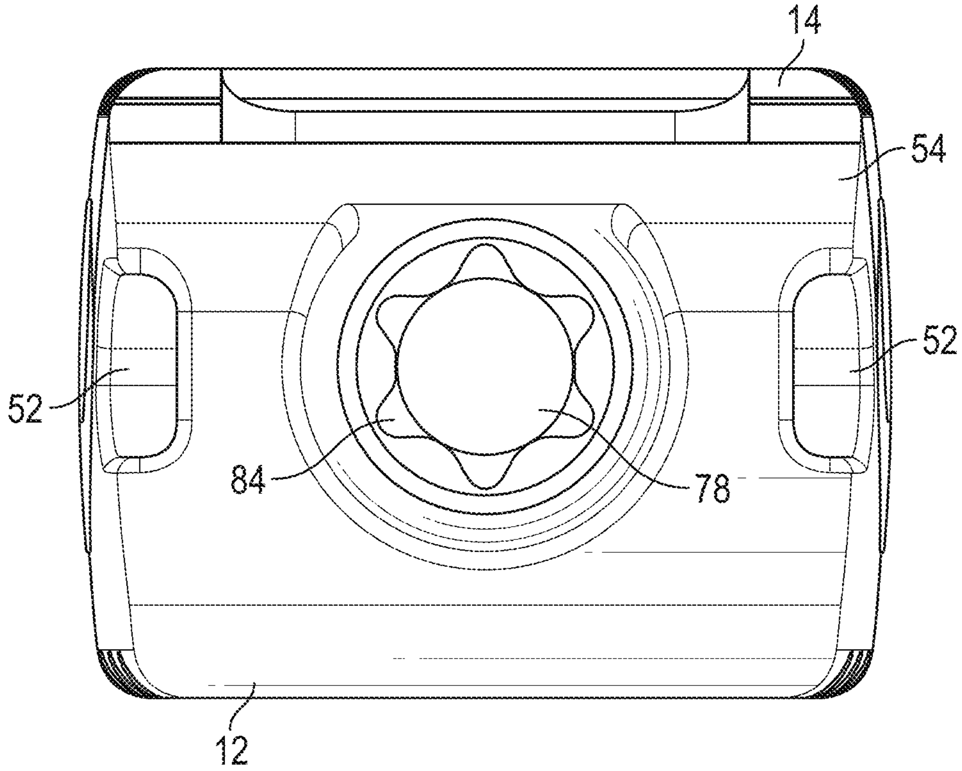
FIG. 13 is a rear view of the implant of FIG. 1 according to one embodiment.

Referring now to FIGS. 12 and 13, a front and rear view, respectively, of the implant 10 are shown. As shown, in the collapsed position, the upper support 14 and the lower support 12 form a bull shaped nose that receives the end cap 18 at the front of the implant 10. The bull shaped nose all the implant 10 to be inserted into a desired location before the implant 10 is expanded. As shown in FIG. 13, the control shaft 78 is received by the rear of the implant 10. However, in operation, the head 84 is positioned away from the rear end of the implant 10, and is at least partially received by the control member bore 44 in the lower support 12.

As utilized herein, the terms "approximately," "about," "substantially", and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the disclosure as recited in the appended claims.

It should be noted that the term "exemplary" and variations thereof, as used herein to describe various embodiments, are intended to indicate that such embodiments are possible examples, representations, or illustrations of possible embodiments (and such terms are not intended to connote that such embodiments are necessarily extraordinary or superlative examples).

The term "coupled" and variations thereof, as used herein, means the joining of two members directly or indirectly to one another. Such joining may be stationary (e.g., permanent or fixed) or moveable (e.g., removable or releasable). Such joining may be achieved with the two members coupled directly to each other, with the two members coupled to each other using a separate intervening member and any additional intermediate members coupled with one another, or with the two members coupled to each other using an intervening member that is integrally formed as a single unitary body with one of the two members. If "coupled" or variations thereof are modified by an additional term (e.g., directly coupled), the generic definition of "coupled" provided above is modified by the plain language meaning of the additional term (e.g., "directly coupled" means the joining of two members without any separate intervening member), resulting in a narrower definition than the generic definition of "coupled" provided above. Such coupling may be mechanical, electrical, or fluidic.

The term "or," as used herein, is used in its inclusive sense (and not in its exclusive sense) so that when used to connect a list of elements, the term "or" means one, some, or all of the elements in the list. Conjunctive language such as the phrase "at least one of X, Y, and Z," unless specifically stated otherwise, is understood to convey that an element may be either X, Y, Z; X and Y; X and Z; Y and Z; or X, Y, and Z (i.e., any combination of X, Y, and Z). Thus, such conjunctive language is not generally intended to imply that certain embodiments require at least one of X, at least one of Y, and at least one of Z to each be present, unless otherwise indicated.

References herein to the positions of elements (e.g., "top," "bottom," "above," "below") are merely used to describe the orientation of various elements in the FIGURES. It should be noted that the orientation of various elements may differ according to other exemplary embodiments, and that such variations are intended to be encompassed by the present disclosure.

Although the figures and description may illustrate a specific order of method steps, the order of such steps may differ from what is depicted and described, unless specified differently above. Also, two or more steps may be performed concurrently or with partial concurrence, unless specified differently above. All such variations are within the scope of the disclosure.

It is important to note that the construction and arrangement of the expandable implant as shown in the various exemplary embodiments is illustrative only. Additionally, any element disclosed in one embodiment may be incorporated or utilized with any other embodiment disclosed herein. It should be appreciated that elements of the various embodiments may be incorporated or utilized with any of the other embodiments disclosed herein.

What is claimed is:

1. An expandable implant comprising:

a first support;

a second support movably coupled to the first support and comprising a control aperture and a surface configured to engage bone, wherein the control aperture is defined by the second support and extends through the surface; and a control assembly comprising:

a control shaft;

a base member received on the control shaft and configured to translate along the control shaft; and a first pivot member pivotally coupled to the base member;

wherein translation of the base member along the control shaft causes a first ramp surface of the first pivot member to engage a ramp surface defining the control aperture to move the first pivot member within the control aperture, and the first support to move relative to the second support to change an angle between the first support and the second support.

2. The expandable implant of claim 1, wherein the first support and the first pivot member are aligned via an interface comprising an alignment projection slidably received in an alignment channel.

3. The expandable implant of claim 1, further comprising a second pivot member coupled to the base member, the first pivot member and the second pivot member coupled to opposite sides of the base member.

4. The expandable implant of claim 3, wherein the first pivot member and the second pivot member are independently rotatable relative to the base member.

5. The expandable implant of claim 3, wherein the first pivot member is received on a first boss on a first side of the base member and the second pivot member is received on a second boss on a second side of the base member.

6. The expandable implant of claim 1, wherein the second support comprises an inner housing defining a cavity and providing access to an interior of the expandable implant.

7. The expandable implant of claim 6, wherein the second support defines an access bore providing tool access to the control shaft via the access bore and the cavity, wherein the cavity is located between the access bore and the control shaft.

8. The expandable implant of claim 6, wherein the control shaft comprises a head received by the inner housing.

9. An expandable implant comprising:

a first support comprising opposing sidewalls, each sidewall comprising an interior ramped surface;

a second support movably coupled to the first support;

a control shaft rotatably coupled to the first support;

a base member coupled to the control shaft and configured to move relative to the control shaft; and a pivot member rotatably coupled to the base member, wherein the pivot member comprises a first ramp surface and a second ramp surface configured to engage the interior ramped surfaces of the first support, and wherein the pivot member is configured to rotate relative to the second support and translate relative to the first support as the base member moves relative to the control shaft.

10. The expandable implant of claim 9, wherein at least one sidewall of the first support and the pivot member are aligned via an interface comprising an alignment projection slidably received in an alignment channel.

11. The expandable implant of claim 9, further comprising an end cap coupled to the second support, wherein an end portion of the control shaft is rotatably received by the end cap, and a head portion of the control shaft is rotatably received by the second support.

12. The expandable implant of claim 9, wherein the pivot member comprises first and second pivot members coupled to opposite sides of the base member.

13. The expandable implant of claim 9, wherein the second support comprises a housing defining a cavity and a control member bore, wherein the control member bore receives a head of the control shaft.

14. The expandable implant of claim 13, wherein the base member is threadingly received on a threaded portion of the control shaft, and wherein the cavity is positioned on an opposite side of the head of the control shaft from the threaded portion.

15. The expandable implant of claim 9, wherein the second support comprises a shoulder portion configured to engage the base member to limit an amount of travel of the base member and an amount of movement of the first support relative to the second support.

16. An expandable implant comprising:

a lower support;

an upper support movably coupled to the lower support, the upper support comprising a first surface configured to engage bone and a control aperture defined by the upper support and extending through the first surface;

a control shaft rotatably coupled to the lower support, wherein the control shaft includes a head configured to receive a tool, wherein manipulation of the control shaft causes relative movement between the upper support and the lower support;

a base member coupled to the control shaft;

a pivot member coupled to the base member and slidingly received within the control aperture, the pivot member comprising a first ramp surface configured to engage a second ramp surface of the control aperture;

a first pivot pin extending through a first side of the upper support and into the lower support; and a second pivot pin extending through a second side of the upper support opposite the first side of the upper support and into the lower support.

17. The expandable implant of claim 16, wherein the control shaft is translationally fixed relative to the lower support.

18. The expandable implant of claim 16, wherein the expandable implant defines a cavity providing access to an interior of the expandable implant.

19. The expandable implant of claim 16, wherein the second ramp surface defines the control aperture such that the pivot member is slidingly received in the control aperture.

20. The expandable implant of claim 16, wherein the base member includes a flat bottom surface that slidingly engages a second surface of the lower support.

* * * * *